United States Patent [19]

Mina et al.

[11] Patent Number: 4,992,597

[45] Date of Patent: Feb. 12, 1991

[54] ANTIOXIDANT PROCESS

[75] Inventors: George L. Mina; Gary D. Heidebrecht, both of Orangeburg, S.C.

[73] Assignee: Ethyl Corporation, Richmond, Va.

[21] Appl. No.: 411,654

[22] Filed: Sep. 25, 1989

[51] Int. Cl.$^5$ .............................................. C07C 39/12
[52] U.S. Cl. ................................ 568/720; 568/717; 568/718; 568/719
[58] Field of Search ............... 568/717, 718, 719, 720

[56] References Cited

U.S. PATENT DOCUMENTS

| | | | |
|---|---|---|---|
| 3,644,538 | 2/1972 | Stanes | 568/720 |
| 3,925,488 | 12/1975 | Shin | 568/720 |
| 4,259,534 | 9/1981 | Gurvich et al. | 568/720 |
| 4,415,409 | 11/1983 | Zudkevitch et al. | 568/913 |
| 4,870,214 | 9/1989 | Mina et al. | 568/720 |
| 4,898,994 | 2/1990 | Livingston et al. | 568/720 |

FOREIGN PATENT DOCUMENTS

| | | | |
|---|---|---|---|
| 0092237 | 7/1981 | Japan | 568/720 |
| 197708 | 9/1977 | U.S.S.R. | 568/913 |

*Primary Examiner*—Werren B. Lone
*Attorney, Agent, or Firm*—Joseph D. Odenweller; Patricia J. Hogan

[57] ABSTRACT

3,5-dialkyl-4-hydroxybenzyl-substituted benzene compounds are made by reacting 2,6-dialkyl-4-methoxymethyl phenols with a benzene compound having an unsubstituted nuclear position in an inert solvent and in the presence of an organic sulfonic acid catalyst while distilling methanol by-product from the reaction mixture as it forms.

19 Claims, No Drawings

ANTIOXIDANT PROCESS

BACKGROUND

Rocklin et al. U.S. Pat. No. 3,026,264 describes the antioxidant use of several 3,5-dialkyl-4-hydroxybenzyl-substituted benzene compounds such as 2,4,6-tri(3,5-di-tert-butyl-4-hydroxybenzyl) mesitylene. They are made by the reaction of 2,6-dialkyl-4-hydroxymethyl phenols with a benzene compound in an inert solvent at −15° to 100° C. in the presence of sulfuric acid or a Friedel Crafts catalyst. Shin U.S. Pat. No. 3,925,488 shows the same reaction except using an organic sulfonic acid catalyst and distilling water from the reaction.

Gurvich et al. G.B. 1,327,542 discloses a process for making 2,4,6-tri(3,5-dialkyl-4-hydroxybenzyl)benzenes by reacting a 2,6-dialkyl-4-methoxymethylphenol with an alkylbenzene compound in an inert solvent in the presence of an acidic catalyst such as sulfuric acid or toluene sulfonic acid. In Example 7, Gurvich et al. used 3.1 moles of toluene sulfonic acid per mole of 2,6-di-tert-butyl-4-methoxymethylphenol. In a commercial operation this presents a severe spent acid disposal problem. However, merely reducing the amount of sulfonic acid results in a reaction wherein less than all of the reactive positions on the benzene compound become substituted. In the case of mesitylene and 2,6-di-tert-butyl-4-methoxymethylphenol, lowering the amount of sulfonic acid gives a product which contains both mono- and di-(3,5-di-tert-butyl-4-hydroxybenzyl) substituted mesitylene by-products, making it unacceptable for commercial sale. Thus, a need exists for a process which allows reduction in the amount of acid used as catalyst and at the same time gives a product suitable for commercial use.

SUMMARY

It has now been discovered that the reaction of a 2,6-dialkyl-4-methoxymethylphenol with a benzene compound such as mesitylene can be effectively catalyzed using catalytic amounts of organic sulfonic acid by conducting the reaction under temperature and pressure conditions that cause the methanol formed during the reaction to distill out of the reaction mixture as it is formed.

DESCRIPTION OF THE PREFERRED EMBODIMENTS

A preferred embodiment of the invention is a process for making a compound having the structure:

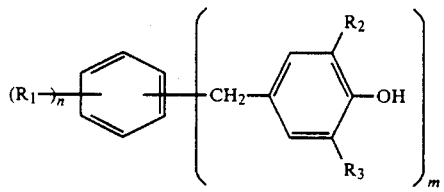

by reacting a reactant having the structure:

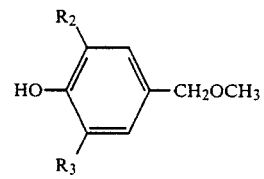

with a benzene compound having the structure:

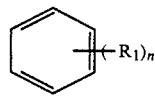

wherein $R_1$ is a $C_{1-3}$ lower alkyl and $R_2$ and $R_3$ are independently selected from the group consisting of $C_{1-8}$ alkyl, $C_{5-8}$ cycloalkyl and $C_{7-12}$ aralkyl, n is zero or an integer from 1 to 4, m is an integer from 2 to 3, and m+n does not exceed 6, in an inert solvent in the presence of an organic sulfonic acid at a temperature of about 20°–150° C. and at a pressure such that methanol by-product formed in the reaction distills out of the reaction mixture as it is formed.

In describing the present invention, the word "alkyl" in 2,6-dialkyl-4-methoxymethylphenol includes cycloalkyls and arylalkyls and the two alkyls on each such reactant can be the same or different.

Useful 2,6-dialkyl-4-methoxymethyl phenols include:
2,6-dimethyl-4-methoxymethylphenol
2-methyl-6-tert-butyl-4-methoxymethylphenol
2,6-diisopropyl-4-methoxymethylphenol
2,6-diisobutyl-4-methoxymethylphenol
2,6-di-tert-butyl-4-methoxymethylphenol
2,6-di-sec-butyl-4-methoxymethylphenol
2-methyl-6-tert-octyl-4-methoxymethylphenol
2-methyl-6-cyclopentyl-4-methoxymethylphenol
2,6-dicyclopentyl-4-methoxymethylphenol
2,6-dicyclohexyl-4-methoxymethylphenol
2-tert-butyl-6-cyclooctyl-4-methoxymethylphenol
2,6-dibenzyl-4-methoxymethylphenol
2-methyl-6-benzyl-4-methoxymethylphenol
2,6-di-(α-methylbenzyl)-4-methoxymethylphenol
2-methyl-6-(α-methylbenzyl)-4-methoxymethylphenol
2-isopropyl-6-(α,α-dimethylbenzyl)-4-methoxymethylphenol.

The most preferred 2,6-dialkyl-4-methoxymethyl phenol is 2,6-di-tert-butyl-4-methoxymethylphenol.

Suitable benzene compounds include benzene and $C_{1-3}$ alkyl-substituted benzenes such as toluene, m-xylene, p-xylene, durene, mesitylene, ethylbenzene, 1,3-diethylbenzene benzene, 1,4-diisopropylbenzene and the like. The preferred benzene compounds are the methyl-substituted benzenes such as durene and especially mesitylene.

Useful solvents include any normally liquid material that is substantially inert under reaction conditions. Such solvents include aliphatic and cycloaliphatic hydrocarbons as well as aliphatic and aromatic halohydrocarbons. Representative examples are cyclohexane, heptane, octane, isooctane, nonane, dichloromethane, chloroform, carbon tetrachloride, 1,2-dichloroethane, dibromoethane and the like.

The most preferred inert solvents are the normally liquid aliphatic and aromatic halohydrocarbons boiling in the range of 40°–200° C. More preferably the halohydrocarbon will boil in the range of 50°–150° C. at atmospheric pressure. Representative examples of such solvents are 1,2-dichloroethane, 1,1-dichloroethane, 1,1,1-trichloroethane, 1,1,2-trichloroethane, 1,1,2-trichloropropane, 1,1,2,2-tetrachloroethane, dibromomethane, chlorobenzene, chloroform, carbon tetrachloride 1,1-dibromoethane, 1,2-dibromoethane, 1,1,1,2-tetrachloroethane and the like. The most preferred solvent is 1,1,-trichloroethane The amount of solvent should be a solvent amount. This is an amount that will hold the 2,6-dialkyl-4-methoxymethylphenol and benzene compound in solution. A useful range is about 500–1000 parts by weight inert solvent per each 100 parts of total benzene compound plus 2,6-dialkyl-4-methoxymethylphenol.

In a more preferred embodiment, only part of the solvent (e.g., 25–50 weight percent) is placed in the reaction vessel together with the benzene compound and organic sulfonic acid. The remainder is used as a solvent for the 2,6-dialkyl-4-methoxymethylphenol being added to the reactor.

The mole ratio of 2,6-dialkyl-4-methoxymethylphenol to benzene compounds depends on the number of 3,5-dialkyl-4-hydroxybenzyl groups to be introduced into the benzene compound. The moles of 2,6-dialkyl-4-methoxymethylphenol should be 100–130% of the stoichiometric amount. With durene the stoichiometric amount is 2 moles per mole of durene and with mesitylene the stoichiometric amount is 3 moles per mole of mesitylene. A preferred amount is about 110–120% of the stoichiometric amount.

Suitable organic sulfonic acids include both aliphatic and aromatic sulfonic acids. Some representative examples of aliphatic sulfonic acids are methane sulfonic acid, ethane sulfonic acid, propane sulfonic acid, trichloromethane sulfonic acid, trifluoromethane sulfonic acid and the like. Representative examples of aromatic sulfonic acids are benzene sulfonic acid, ortho, meta and para toluene sulfonic acid, chlorobenzene sulfonic acid, chlorotoluene sulfonic acid and the like. The more preferred organic sulfonic acids are methane sulfonic acid, ethane sulfonic acid and toluene sulfonic acids including mixtures thereof.

The amount of organic sulfonic acid is a catalytic amount. The prior art used about 3.1 moles toluene sulfonic acid per mole of 2,6-dialkyl-4-methoxymethyl phenol. The present process permits the use of less sulfonic acid than required by the prior art methods. A useful range is about 0.005–1.0 mole organic sulfonic acid per mole of 2,6-dialkl-4-methoxymethylphenol. A more preferred amount is about 0.01–0.5 mole organic sulfonic acid and still more preferably about 0.015–0.1 mole organic sulfonic acid per mole of 2,6-dialkyl-4-methoxymethylphenol. A most preferred range is 0.03–0.05 mole organic sulfonic acid per mole of 2,6-dialkyl-4-methoxymethylphenol.

The reaction will proceed over a wide temperature range. A useful range in which to experiment is about 0°–150° C. A more preferred range is about 10°–80° C. and a most preferred range is 15°–40° C.

The reactor should be fitted to permit distillation of a methanol-containing distillate from the reaction mixture while feeding the 2,6-dialkyl-4-methoxymethylphenol. Depending on reaction temperature, it is usually necessary to lower the reactor pressure to cause the distillation. With a 1,1,1-trichloroethane solvent at 20° C., the solvent/methanol mixture distilled at 100 torr. At 150 torr, the mixture refluxed at 30°–35° C. Solvents having a normal boiling point above about 70° C. are more efficient in removing methanol without with codistilling a large amount of inert solvent.

The distillate removed can be merely discarded and replaced by the solvent being added with the 2,6-dialkyl-4-methoxymethylphenol solution. Preferably the distillate is treated to remove methanol and then recycled to the reaction mixture. One way to do this is to pass the distillate through an adsorbent which has an affinity for methanol. Zeolites can perform this function. Although both natural and synthetic zeolites can be used, the synthetic zeolites are preferred. The "A" type zeolites are effective, especially type 4A zeolite.

Better results are obtained when the 2,6-dialkyl-4-methoxymethylphenol is fed to the inert solvent containing the benzene compound and organic sulfonic acid catalyst over an extended period of time to prevent the accumulation of a large amount of 2,6-dialkyl-4-methoxymethylphenol in the reaction mixture. Feed time will depend upon scale and rate of methanol removal. A useful time range in which to experiment to optimize results is about 0.5–12 hours. A more preferred feed period is 1–8 hours The following example shows the best mode known to the inventors for carrying out the process.

EXAMPLE 1

In a glass reaction flask was placed 35 mL 1,1,1-trichloroethane, 0.08 g (0.0008 mole) of methane sulfonic acid and 1.18 g (0.01 mole) of mesitylene. The flask was equipped with a stirrer, thermometer, pressure equalized addition funnel and a reflux condenser that drained all condensate down through a bed of type 4A zeolite. The addition funnel was filled with a solution of 8.37 g (0.033 mole) 2,6-di-tert-butyl-4-methoxymethylphenol in 35 mL 1,1,1-trichloroethane. The stirred reaction mixture was warmed to 40° C. and the pressure reduced to about 220 torr. Feed of 2,6-di-tert-butyl-4-methoxymethylphenol was started while a methanol-containing distillate formed. The condensed distillate was drained down through the bed of type 4A zeolite and back into the reaction flask. Feed time was two hours. During the feed, another 0.14 g of methane sulfonic acid was added in two portions (total added 0.22 g, 0.0013 mole). GC analysis of the final reaction mixture excluding solvent was

| | |
|---|---|
| 2,4,6-tri-(3,5-di-tert-butyl-4-hydroxybenzyl) mesitylene | 92.11% |
| 2,4-di-(3,5-di-tert-butyl-4-hydroxybenzyl) mesitylene | 1.39% |
| 4,4-methylenebis(2,6-di-tert-butylphenol) | 5.47% |

The product was recovered by crystallization and filtration.

We claim:
1. A process for making a compound having the structure:

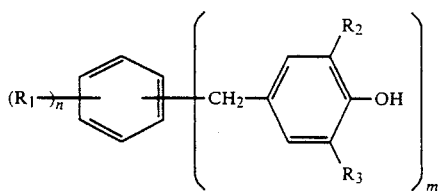

by reacting a reactant having the structure:

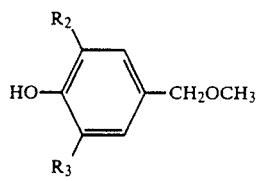

with a benzene compound having the structure:

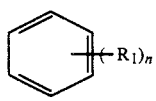

wherein $R_1$ is a $C_{1-3}$ lower alkyl and $R_2$ and $R_3$ are independently selected from the group consisting of $C_{1-8}$ alkyl, $C_{5-8}$ cycloalkyl and $C_{7-12}$ aralkyl, n is zero or an integer from 1 to 4, m is an integer from 2 to 3, and m+n does not exceed 6, in an inert solvent in the presence of an organic sulfonic acid at a temperature of about 10°–150° C. and at a pressure such that methanol by-product formed in the reaction distills out of the reaction mixture as a methanol-containing distillate as it is formed.

2. A process of claim 1 wherein said inert solvent is an aliphatic or aromatic normally liquid halohydrocarbon.

3. A process of claim 2 wherein said benzene compound is mesitylene.

4. A process of claim 3 wherein said reactant is 2,6-di-tert-butyl-4-methoxymethylphenol.

5. A process of claim 4 wherein said inert solvent is a normally liquid chlorohydrocarbon having a normal boiling range of about 40°–200° C.

6. A process of claim 4 wherein said inert solvent is a normally liquid chlorohydrocarbon having a normal boiling range of about 50°–150° C.

7. A process of claim 1 wherein the amount of said organic sulfonic acid is about 0.005–1.0 mole per mole of said reactant.

8. A process of claim 7 wherein said organic sulfonic acid is an aromatic sulfonic acid.

9. A process of claim 8 wherein said aromatic sulfonic acid is toluene sulfonic acid.

10. A process of claim 9 wherein said inert solvent is a normally liquid aliphatic chlorohydrocarbon having a normal boiling point of about 40°–200° C.

11. A process of claim 10 wherein said reactant is 2,6-di-tert-butyl-4-methoxymethylphenol and said benzene compound is mesitylene.

12. A process of claim 7 wherein said organic sulfonic acid is a $C_{1-2}$ alkane sulfonic acid.

13. A process of claim 12 wherein said inert solvent is a normally liquid aliphatic chlorohydrocarbon having a boiling point of about 40°–200° C.

14. A process of claim 13 wherein said reactant is 2,6-di-tert-butyl-4-methoxymethylphenol and said benzene compound is mesitylene.

15. A process for making 2,4,6-tri(3,5-di-tert-butyl-4-hydroxybenzyl) mesitylene, said process comprising (a) placing a solvent amount of a chlorohydrocarbon having a normal boiling point of about 40°–150° C. and about 1 mole part of mesitylene and about 0.05–0.2 mole part of a catalyst selected from methane sulfonic acid, ethane sulfonic acid or mixtures thereof in a reaction vessel, (b) feeding about 3.1–3.4 mole parts of 2,6-di-tert-butyl-4-methoxymethylphenol to said reaction vessel over an extended period of about 0.5–12 hours while the vessel contents are at a temperature of about 20°–60° C. while maintaining said reaction vessel at a reduced pressure at which a methanol-containing distillate distills from the reaction mixture (c) distilling said methanol-containing distillate from said reaction mixture and (d) recovering said 2,4,6-tri-(3,5-di-tert-butyl-4-hydroxybenzyl) mesitylene.

16. A process of claim 15 wherein said chlorohydrocarbon is a trichloroethane or mixture of trichloroethanes.

17. A process of claim 15 wherein said methanol-containing distillate from step (c) is contacted with a zeolite adsorbent having an affinity for methanol to form a methanol-depleted distillate and recycling said methanol-depleted distillate to said reaction mixture 18. A process of claim 17 wherein said zeolite is a type 4A zeolite.

19. A process of claim 18 wherein said catalyst is methane sulfonic acid.

* * * * *